United States Patent [19]

Dolphin et al.

[11] Patent Number: 5,780,622
[45] Date of Patent: Jul. 14, 1998

[54] METHOD OF SYNTHESIZING 5,15-DIARYLBENZOCHLORIN-7-ONE COMPOUNDS

[75] Inventors: David Dolphin; Ross Boyle, both of Vancouver, Canada

[73] Assignee: The University of British Columbia, Vancouver, Canada

[21] Appl. No.: 909,136

[22] Filed: Aug. 11, 1997

Related U.S. Application Data

[62] Division of Ser. No. 235,174, Apr. 29, 1994, Pat. No. 5,656,756.
[51] Int. Cl.[6] .................................... C07D 487/22
[52] U.S. Cl. ......................... 540/472; 540/145; 540/465; 540/474
[58] Field of Search ........................ 540/472, 465, 540/474, 145

[56] References Cited

U.S. PATENT DOCUMENTS 5,656,756  8/1997  Dolphin et al. .................. 540/472

Primary Examiner—Mukund J. Shah
Assistant Examiner—Pavanaram K. Sripada
Attorney, Agent, or Firm—Kate H. Murashige

[57] ABSTRACT

A novel 5,15-diarylbenzochlorin-7-one compound having the formula (I) or (II):

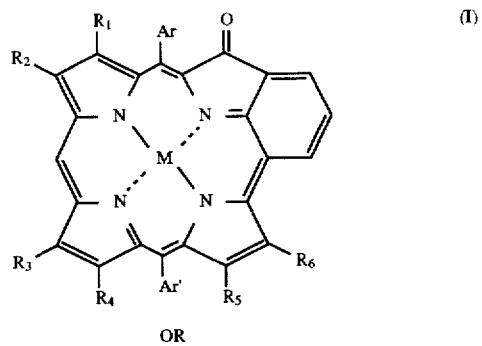

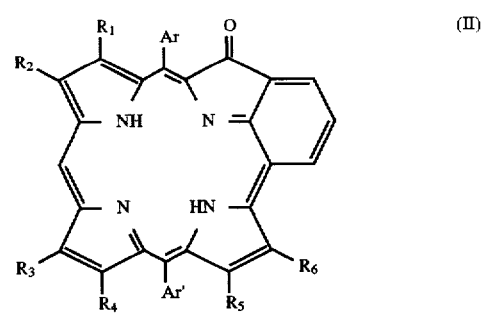

wherein M is a metal. A novel method for synthesizing the compound of formula (I) comprises the steps of:
 a. cyclizing a meso-(formylvinyl) 5,15-diarylporphyrin to form a cyclization reaction mixture, and
 b. oxidizing said reaction mixture to form the 5,15-diarylbenzochlorin-7-one of formula (I).

A novel method for synthesizing the compound of formula (II) comprises the cyclizing and oxidizing steps listed above and, either prior to or after the oxidizing step, adding the step of demetallating the compound.

11 Claims, 3 Drawing Sheets

METHOD OF SYNTHESIZING 5,15-DIARYLBENZOCHLORIN-7-ONE COMPOUNDS

This application is a divisional of application Ser. No. 08/235,174, filed Apr. 29, 1994, which is issued as U.S. Pat. No. 5,656,756 on Aug. 12, 1997.

FIELD OF THE INVENTION

The present invention relates to certain benzochlorinone compounds and their preparation. In particular, the invention relates to the synthesis of these compounds that have been substituted in the 5- and 15-positions with an aromatic ring. Many of these compounds are useful photosensitizers in the field of photodynamic therapy ("PDT") for mediating the destruction of unwanted cells or tissues or other undesirable materials by irradiation.

BACKGROUND ART

In the field of PDT, various tetrapyrrolic purpurins, chlorins, phthalocyanines and benzochlorins have shown the ability both to localize at a tumor site and to absorb light to form an activated state in response to the light. Of particular interest are the compounds which absorb light in the red region of the spectrum (600 to 800 nm), which more easily penetrates bodily tissues. Thus, the various functionalities of these photosensitizers can be altered to increase the efficiency of tumor necrosis. One class of these red-absorbing compounds is the 5,15-(p-substituted)diaryl benzochlorins, and related formyl-substituted porphyrins, which display major absorptions in the 500–710 nm region.

It is known that nickel(II) or copper(II) porphyrins, such as copper(II) octaethylporphyrin, may be treated with 3-(dimethylamino)acrylaldehyde ("3-DMA") and phosphoryl chloride (POCl₃) to form the corresponding meso-(2-formylvinyl)porphyrins. These reactions are commonly known as Vilsmeier Reactions. Further, when these compounds are subjected to strong acid treatment, the aldehyde portion cyclizes to form a fused benzene ring, giving the corresponding benzochlorins, as shown below:

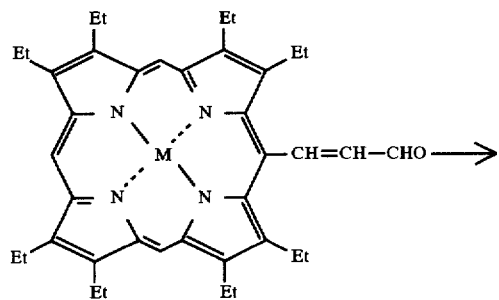

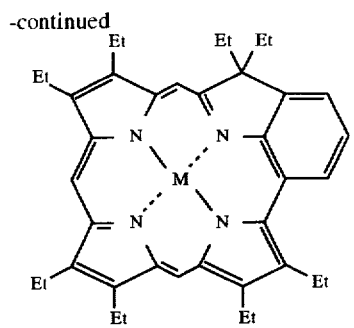

-continued where M is Ni or Cu. Arnold et al., "Wittig Condensation Products from Nickel meso-Formyl-octaethylporphyrin and -aetioporphyrin I and Some Cyclisation Reactions," *J. C. S. Perkin I*, 1660–70 (1978); Vicente et al., "Efficient New Syntheses of Benzochlorins, Benzoisobacteriochlorins, and Benzobacteriochlorins," *Tetrahedron Letters*, 31, 1365–68 (1990); and Vicente et al., "Vilsmeier Reactions of Porphyrins and Chlorins with 3-(Dimethylamino)acrolein to Give meso-(2-Formylvinyl)porphyrins: New Syntheses of Benzochlorins, Benzoisobacteriochlorins, and Benzobacteriochlorins and Reductive Coupling of Porphyrins and Chlorins Using Low-Valent Titanium Complexes," *J. Org. Chem.* 56, 4407–18 (1991).

Recently, 5,15-diaryl porphyrins have been treated with the Vilsmeier reagent (3-DMA/POCl₃) to form the corresponding meso-(2-formylvinyl)porphyrins, which have been cyclized to form the corresponding benzochlorins substituted with two aryl rings, one in the 5-position and the other in the 15-position. Osuka et al., "Synthesis of Benzochlorin Monomer, Dimer, and Porphyrin-Benzochlorin Heterodimer from 5-Aryl- and 5,15-Diaryl-octaethylporphyrins," *Bull. Chem. Soc. Jpn.*, 65, 3322–30 (1992). Some of these derivatives have shown strong absorptions in the visible region around 700 nm, due to the modification of the porphyrin chromophore. Further, the presence of the two aryl rings on the structures of these compounds allows for flexibility in design to adjust for such properties as hydrophobicity, water solubility, and electrochemical and photophysical properties. Gunter, "5,15-Diaryl Substituted Benzochlorins—Synthesis and Structure," *Tetrahedron* 47, 7853–68 (1991).

In all of the above-described methods, however, the presence of substituents at the pyrrolic β-positions adjacent to the benzenoid ring formed in the cyclization reaction causes the formation of a product that is either dialkyl substituted or hydroxyalkyl substituted at the β-position. When there are no substituents at either of the peripheral β-positions where the benzenoid ring will be formed during cyclization, ring closure causes the formation of a reaction mixture containing more than one compound, probably including, among other things, a secondary alcohol intermediate as opposed to a tertiary alcohol. This intermediate reaction mixture is then susceptible to oxidation to form a ketone. Thus, it has now been discovered that, in this way, a carbonyl chromophoric unit can be added to the benzochlorin nucleus, causing an even further bathochromic shift and an improved intensification of the Q band of longest wavelength.

DISCLOSURE OF THE INVENTION

According to the present invention, there has been found a novel 5,15-diarylbenzochlorin-7-one compound having the formula (I) or (II):

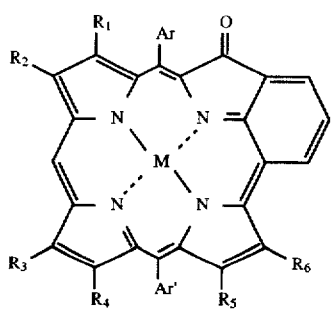

(I)

OR

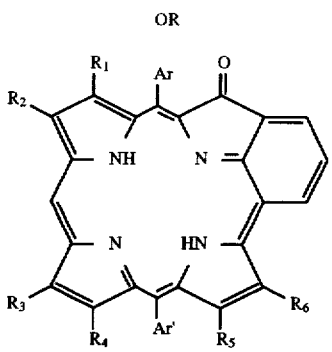

(II)

wherein M is a metal selected from the group consisting of Ni(II), Cu(II), Zn, Sn, Ge, Si, Ga and Al;

$R_1$ through $R_6$ are independently a hydrogen atom, a lower alkyl group, a lower alkyl carboxylic acid or acid ester group or, taken together with another ring or meso-substituent or another $R_1$ or $R_2$, form a fused 5- or 6-membered ring; and Ar and Ar' are aromatic rings, which may be the same or different.

Further, a method has been found for synthesizing compounds of formula (I) and (II) more efficiently and with greater than usual purity. Specifically, a method of making a compound having formula (I) comprises the steps of:

a. cyclizing a meso-(formylvinyl) 5,15-diphenylporphyrin having the formula (III)

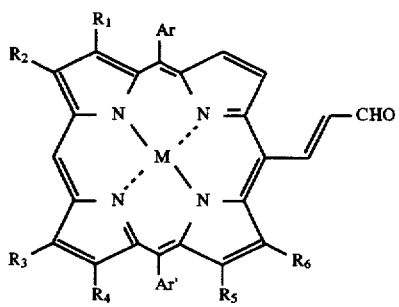

(III)

to form a cyclization reaction mixture; and b. oxidizing the cyclization reaction mixture to form the 5,15-diphenylbenzochlorin-7-one of formula (I).

Two methods of making the demetallated compounds of formula (II) are disclosed. The first comprises the steps of:

a. cyclizing a meso-(formylvinyl) 5,15-diarylporphyrin having the formula (III) to form a cyclization reaction mixture;

b. oxidizing the cyclization reaction mixture to form the 5,15-diarylbenzochlorin-7-one of formula (I); and c. demetallating the 5,15-diarylbenzochlorin-7-one of formula (I) to form the demetallated 5,15-diarylbenzochlorin-7-one of formula (II).

The second method of making a demetallated compound of formula (II) comprises the steps of:

a. cyclizing a meso-(formylvinyl) 5,15-diarylporphyrin having the formula (III) to form a cyclization reaction mixture;

b. demetallating the cyclization reaction mixture to form a demetallation reaction mixture; and c. oxidizing the demetallation reaction mixture to form the 5,15-diarylbenzo-chlorin-7-one of formula (II).

BRIEF DESCRIPTION OF DRAWINGS

The present invention will be more clearly understood by referring to the following drawings, in which.

MODES OF CARRYING OUT THE INVENTION

Figure 1:
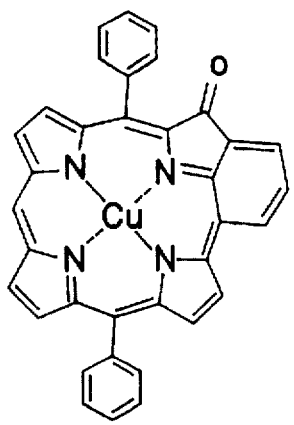
FIG. 1 shows the absorbance spectrum of Cu(II) 5,15-diphenylbenzochlorin-7-one.
Figure 1:
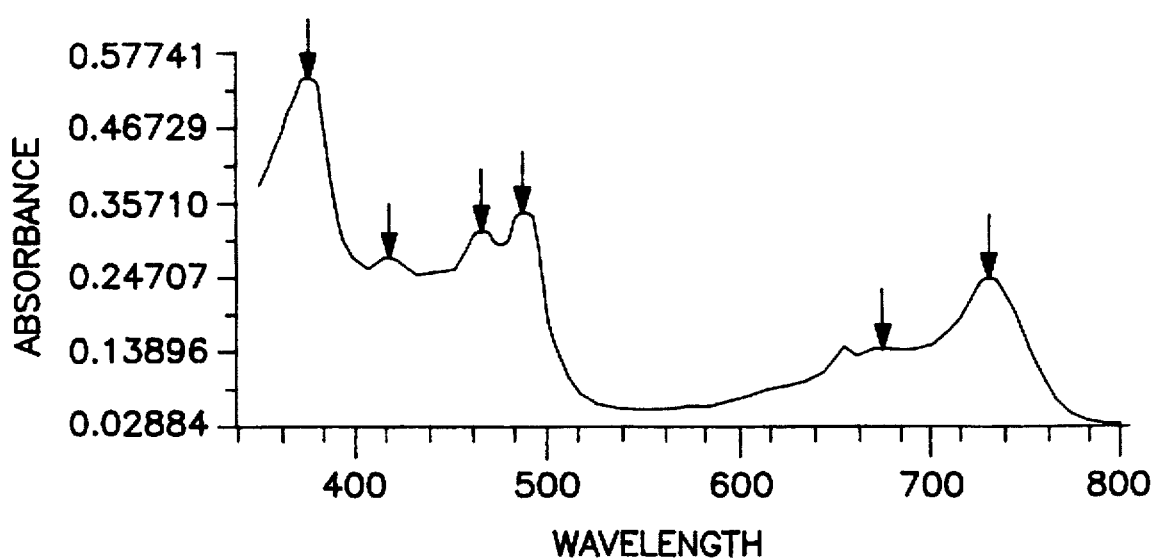

The 5,15-diarylbenzochlorin-7-one compounds of the invention have formula (I) or formula (II), as described and shown above. M in formula (I) can be any metal species that is capable of forming the complex of formula (I), but is preferably selected from the group consisting of Ni(II), Cu(II), Zn, Sn, Ge, Si, Ga and Al. Most preferably, M is Ni(II) or Cu(II).

$R_1$ through $R_6$ can be any one of a large number of substituents, so long as they do not interfere with the cyclizing and oxidation steps outlined above. Preferably, $R_1$ through $R_6$ are independently a hydrogen atom; a lower alkyl group, such as methyl, ethyl, n-propyl, isopropyl, t-butyl and n-pentyl; a lower alkyl carboxylic acid, such as carboxymethyl, carboxyethyl, carboxy-n-butyl, carboxy-sec-butyl, carboxy-n-hexyl; or a carboxylic acid ester group, such as $-CH_2CH_2COOCH_3$, $-CH_2CH_2COOCH_2CH_3$, $-CH_2CH(CH_3)COOCH_2CH_3$, $-CH_2CH_2CH_2COOCH_2CH_2CH_3$, $-CH_2CH(CH_3)_2 COOCH_2CH_3$, or the like.

Further, $R_1$ and $R_2$, $R_3$ and $R_4$, or $R_5$ and $R_6$, can be taken together with another ring, ring substituent or meso-substituent to form a fused 5- or 6-membered ring. The fused 5- or 6-membered ring so formed may be any saturated or unsaturated, carbocyclic or heterocyclic 5- or 6-membered ring that does not interfere with the ring closure and oxidation reaction steps of the invention. Examples of such rings include cyclopentane, furan, thiophene, pyrrole, isopyrrole, 3-isopyrrole pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiathiazole, 1,2,4-oxadiazole, 1,2,5-oxadiazole, 1,3,4-oxadiazole, 1,2,3-dioxazole, 1,2,4-dioxazole, 1,2,5-oxathiazole, 1,3 oxathiole, benzene, cyclohexane, 1,2-pyran, 1,4-pyran, 1,2-pyrone, 1,4-pyrone, 1,2-dioxin, 1,3-dioxin (dihydro form), pyridine, pyridazine, pyrimidine, pyrazine, piperazine, 1,3,5-triazine, 1,2,4-triazine, 1,2,4-oxazine, 1,3, 2-oxazine, o-isoxazine, 1,2,5-oxathiazine, 1,4-oxazine, p-isoxazine, 1,2,6-oxathiazine, 1,3,5,2-oxadiazine, morpholine, azepine, oxepin, thiepin, 1,2,4-diazepine, and the like. Preferably, when $R_1$ and $R_2$, $R_3$ and $R_4$, or $R_5$ and $R_6$, form a fused, 5- to 6-membered ring, the ring is a 6-membered ring. Most preferably, when $R_1$ and $R_2$, $R_3$ and $R_4$, or $R_5$ and $R_6$, form a ring, it is a 6-membered carbocyclic ring, i.e., a benzene ring.

In a particularly preferred embodiment, $R_1$ through $R_6$ are independently hydrogen, methyl, ethyl, or lower alkyl esters, most preferably being either hydrogen or ethyl.

Ar and Ar' are the same or different and can be any one of a large number of aromatic rings, preferably containing about 5–12 carbon atoms, optionally containing one or more heteroatoms, and optionally including rings that are fused to the existing conjugated porphyrin ring structure. Examples of suitable aromatic rings include furan, thiophene, pyrrole, isopyrrole, 3-isopyrrole, pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxathiazole, 1,3-oxathiole, benzene, 1,2-pyran, 1,4-pyran, 1,2-pyrone, 1,4-pyrone, 1,2-dioxin, 1,3-dioxin, pyridine, pyridazine, pyrimidine, pyrazine, 1,3,5-triazone, 1,2,4-triazine, 1,2,3-triazine, 1,2,4-oxazine, 1,3,2-oxazine, 1,3,6-oxazine, 1,4-oxazine, o-isoxazine, p-isoxazine, 1,2,5-oxathiazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, naphthalene, 1,2-benzopyran, 1,2-benzopyrone, 1,4-benzopyrone, 2,1-benzopyrone, 2,3-benzopyrone, quinoline, isoquinoline, 1,2-benzodiazine, 1,3-benzodianzine, naphthyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, anthracene, phenanthrene, carbazole, xanthene, acridine, purine and the like.

In a particularly preferred embodiment, Ar and Ar' are selected from 5-, 6- and 7-membered aromatic rings, such as pyrrole, pyridine, pyrazine, pyrimidine, benzene, and azepine. In another embodiment, Ar and Ar' are each a pyridine, phenyl or naphthyl ring. Even more preferably, Ar and Ar' each have the formula:

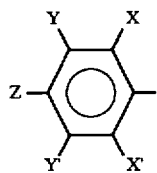

where X, Y, Z, X' and Y' can be any one of a large number of substituents and are generally to "fine tune" the biological activity, the biodistribution, the absorption and clearance characteristics, and the physical properties of the desired product. One way in which this may be done by selecting substituents in such a manner that the compound of formula (I) or (II) is an amphiphilic molecule. By "amphiphilic" is meant the molecule becomes more asymmetric, such as (1) having both (a) a highly polar, water-soluble region and (b) a highly hydrophobic, water-insoluble region;

(2) having both (a) a nonionic region and (b) an ionic region; or (3) having both (a) an anionic portion and (b) a cationic portion.

However, it should be noted that the invention also includes 5,15-benzochlorin-7-one compounds having substantially or exactly symmetrical aryl substituents. Further, any aryl substituent chosen should also have no adverse effect on the ability of the compound to undergo the step "a," and step "b," reactions used to prepare the compounds of the invention.

Preferably, X, X', Y, Y' and Z are independently (1) hydrogen; (2) halogen, such as fluoro, chloro, iodo and bromo; (3) lower alkyl, such as methyl, ethyl, n-propyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid, such as —$CH_2COOH$, —$CH_2CH(Br)COOH$, —$CH_2CH(CH_3)COOH$, —$CH(Cl)$—$CH_2$—$CH(CH_3)$—$COOH$, —$CH_2$—$CH_2$—$C(CH_3)_2$—$COOH$, —$CH_2$—$CH_2$—$CH_2$—$CH_2$—$COOH$, $C(CH_3)_3$—$COOH$, $CH(Cl)_2$—$COOH$ and the like; (7) carboxylic acid ester, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_2CH_3$, —$CH_2CH(CH_3)_2COOCH_2CH_3$, and the like; (8) sulfonic acid ester, such as methyl sulfonate, ethyl sulfonate, cyclohexyl sulfonate, p-tosylate, o-tosylate and the like; (9) amino, such as unsubstituted primary amino, methylamino, ethylamino, n-propylamino, isopropylamino, 5-butylamino, sec-butylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino)heptyl, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (10) cyano; (11) nitro; (12) a biologically active group; or (13) any other substituent that increases the amphiphilic nature of the compound of formula (I) or (II).

The term "biologically active group" can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructofuranose; (5) O-acyl derivatives such as penta-O-acetyl-α-glucose; (6) O-methyl derivatives such as methyl α-glucoside, methyl β-glucoside, methyl α-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, δ-gluconolactone, δ-glucuronolactone, ascorbic acid, and dehydroascorbic acid; (10) phosphoric acid esters such as α-glucose 1-phosphoric acid, α-glucose 6-phosphoric acid, α-fructose 1,6-diphosphoric acid, and α-fructose 6-phosphoric acid; (11) deoxy sugars such as 2-deoxy-ribose, rhamnose (deoxymannose), and fucose (6-deoxy-galactose); (12) amino sugars such as glucosamine and galactosamine; muramic acid and neuraminic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as α-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; and (4) neurotransmitters, such as acetylcholine, serotonin, dopamine, and the like. Any analog of these substances that also succeeds in binding to a biological receptor is also included.

Particularly useful examples of substituents tending to increase the amphiphilic nature of the compound of formula (I) include: (1) long chain alcohols, for example, —$C_{12}H_{24}$—OH where —$C_{12}H_{24}$ is hydrophobic; (2) fatty acids and their salts, such as the sodium salt of the long-chain fatty acid oleic acid; (3) phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; (4) sphingolipids, such as sphingomyelin; and (5) glycolipids, such as glycosyldiacylglycerols, cerebrosides, sulfate esters of cerebrosides or gangliosides.

In a preferred embodiment, X, Y, X' and Y' are each hydrogen, and Z is selected from the group consisting of hydrogen, halogen, lower alkyl, lower alkoxy, hydroxy, carboxylic acid, carboxylic acid ester, sulfonic acid ester (especially aromatic sulfonic acid ester), nitro, amino (especially lower alkyl amino), cyano, and a biologically active group. In another preferred embodiment, X, Y, Z, X' and Y' are selected from the group consisting of hydrogen, methyl, ethyl, t-butyl, methoxy, hydroxy, fluoro, chloro, iodo, bromo, —C(O)—OCH$_3$, amino, and a biologically active group such as a ligand specific for a receptor. In yet another preferred embodiment, X and X' are lower alkyl groups, such as methyl, and Y, Z and Y' are all hydrogen. In still another preferred embodiment, at least one of X, Y, Z, X' and Y' is a biologically active group or a substituent that increases the amphiphilic nature of the molecule.

Step "a." of the process of making the compounds of the invention comprises cyclizing a meso-(formylvinyl) 5,15-diarylporphyrin of formula (III) to form the cyclization reaction mixture. The starting aldehyde for this reaction, meso-(formylvinyl) 5,15-diarylporphyrin, can be prepared by any one of a number of standard procedures for obtaining aldehydes. Examples include such techniques as: (1) oxidizing an appropriate primary alcohol (in this case, the compound of formula (III) having a 3-hydroxyprop-2-enyl meso-substituent in place of the meso-(formylvinyl) substituent); (2) reducing the corresponding acid chloride (the compound of formula (II) having a 3-carboxyprop-2-enyl chloride as a meso-substituent); (3) using a Vilsmeier reagent [3-(dimethylamino)acrylaldehyde ("3-DMA") and phosphoryl chloride (POCl$_3$)] to treat a compound having the ring structure of formula (II) but with an unsubstituted meso-position, in accordance with Gosmann et al., *Angew. Chem., Int. Ed. Engl.* 25, 1100 (1986), the disclosure of which is hereby incorporated by reference; (4) treating the corresponding compound of formula (II) having a mesovinyl substituent with phosphorus oxychloride and N,N-dimethylformamide ("DMF") in accordance with Arnold, "Wittig Condensation Products from Nickel meso-Formyl-octaethylporphyrin and -aetioporphyrin I and Some Cyclisation Reactions", *J. C. S. Perkin I*, 1667–1670 (1988); (5) treating a compound like the compound of formula (II), except for having one or two of the non-aryl-substituted meso positions substituted with one or two halogen atoms, with the appropriate organotributyl tin reagent in the presence of a palladium-based catalyst, in accordance with the procedures described in DiMagno et al., "Facile Elaboration of Porphyrins via Metal-Mediated Cross-Coupling," *J. Org. Chem.* 58, 5983–93 (1993), and DiMagno et al., "Catalytic Conversion of Simple Haloporphyrins into Alkyl-, Aryl-, Pyridyl-, and Vinyl-Substituted Porphyrins", *J. Am. Chem. Soc.* 115, 2513–15 (1993), the disclosures of which are both hereby incorporated by reference; and the like.

Preferably, the compound of formula (III) used as the starting material for step "a." is prepared by using a Vilsmeier reaction to react a 5,15-diaryl porphyrin compound corresponding to formula (II) having an unsubstituted meso-position with 3-DMA and phosphoryl chloride to form a formylvinyl sidechain. A general procedure for carrying out such a reaction is set forth below:

3-DMA is dissolved in a solvent such as 1,2-dichloroethane, and the solution is cooled to a temperature from about −5° to 20° C. First POCl$_3$ and then a solid Cu or Ni porphyrin having at least one unsubstituted meso-position are combined with the reaction mixture. The mixture is warmed to a temperature varying from about room temperature to about 50° C. The progress of the reaction can be monitored closely by thin layer chromatography ("TLC") and allowed to proceed until no more of the porphyrin starting material is consumed, usually about four hours. A saturated solution of sodium acetate is added, and the resulting mixture is stirred vigorously until hydrolysis is complete as judged by TLC (about 0.25 to about 16 hours). The organic phase of the reaction mixture is separated from the aqueous phase and dried over anhydrous sodium sulfate. The solvent is removed by rotary evaporation. The remaining residue is chromatographed on silica gel using dichloromethane as the eluant, and the major fraction is collected. After evaporation of the solvent, the porphyrin product may be recrystallized in an appropriate solvent, or otherwise further purified, if desired.

The cyclization of step "a." can be brought about by any cyclization reagent that causes the reaction of the meso-position vinyl aldehyde with an adjacent β-pyrrole carbon atom, thus forming a fused benzenoid ring with the adjacent pyrrole ring. Typical examples of cyclization reagents include Lewis acids, such as $BF_3$—$O(C_2H_5)_2$, $SnCl_4$, $AlCl_3$, $FeCl_3$, fused zinc chloride, and the like; mineral acids, such as sulfuric acid and hydrochloric acid; other acids, such as acetic acid, trifluoroacetic acid, trichloroacetic acid, trifluoromethane sulfonic acid, and p-toluenesulfonic acid; and mixtures of such cyclization reagents. Examples of particularly useful combinations of acids include (1) a mixture of trifluoroacetic acid and acetic acid at about a 1:1 ratio and (2) a mixture of trifluoroacetic acid and sulfuric acid.

Some of the above acids, such as trifluoroacetic acid and concentrated sulfuric acid, can be used neat. Others are best used in combination with a suitably non-reactive organic solvent to form combinations, such as trifluoroacetic acid in 1,1-dichloroethane, $BF_3$—$O(C_2H_5)_2$ or $SnCl_4$ in 1,1-dichloroethane, sulfuric acid in DMF, and the like. Examples of particularly useful organic solvents include chlorinated solvents such as dichloromethane, 1,1-dichloroethane and methylene chloride; DMF; aromatic solvents, such as toluene and benzene; and ethers, such as diethyl ether, tetrahydrofuran, diethylene glycol and glycol dimethyl ether (ethylene glycol dimethyl ether). When a solvent is used, a chlorinated solvent such as dichloromethane or 1,1-dichloroethane is especially preferred in step "a."

The temperature of the reaction mixture during step "a." can vary widely but, typically, is maintained in the range of about 0° to 1000° C. Preferably, the reaction is carried out at about room temperature. The time required for the cyclization reaction of step "a." will depend to a large extent on the temperature used and the relative reactivities of the starting materials but, typically, varies from about 5 minutes to about 24 hours. Preferably, the reaction time for step "a." is in the range of about 15 minutes to about 5 hours.

The cyclization reaction can be carried out at pressures both above and below atmospheric pressure. Preferably, however, the reaction is carried out at a pressure about equal to atmospheric pressure. The reaction can be carried out in the presence of a mixture of gases approximating air but, when particularly reactive reactants are involved, the gaseous mixture may be enriched with an inert gas, such as nitrogen gas, argon, and the like.

It should be noted that, under most typical cyclization reaction conditions, the reaction often proceeds unacceptably slow or to unacceptably incomplete degree when the metal M is zinc. However, M may be exchanged with other useful metal ions before and/or after the cyclization reaction if a compound of formula (I) where M is zinc is desired. The exchange process is accomplished by demetallation, as described below (for example with $H_2S$-trifluoroacetic acid), followed by re-metallation in accordance with known procedures, for example, by treating with zinc acetate in $CHCl_3$/$CH_3OH$.

The progress of the reaction often involves a color change of the reaction mixture from red to green. If desired, this color change can be used to monitor the approximate degree of completion of the reaction. Other known techniques, such as various types of chromatography, especially TLC, can also be used to follow the progress of the reaction by the disappearance of the starting material.

At the conclusion of the cyclization reaction, a reaction mixture results, which is typically used directly in the oxidation step "b." without the intervening isolation or purification of the intermediate(s) present in the reaction mixture. A general procedure for accomplishing a typical cyclization step is set forth below:

About 0.2 g of a solid meso-(2-formylvinyl) diarylporphyrin (having an adjacent pyrrole ring without β-substituents) is placed under a nitrogen atmosphere in $CH_2Cl_2$ (10 ml), and 100 μL $BF_3$.$O(C_2H_5)_2$ is added. The solution is stirred vigorously for about 1 to 1.5 hour, after which the color of the solution typically changes from red to green.

The oxidation of the cyclization reaction mixture to form the ketone of formula (I) can be accomplished by any of the usual oxidizing agents generally suitable for converting alcohols to ketones. Examples of such useful oxidizing agents include $KMnO_4$, $CrO_3$, $K_2Cr_2O_7$, pyridinium chlorochromate, pyridinium dichromate, copper metal, dichloro-dicyanobenzoquinone ("DDQ"), o- and p-chloranil, $O_2$, trifluoroacetic acid, and the like.

Most of the above oxidizing agents are used in combination with a suitably non-reactive organic or inorganic solvent, such as water, glacial acetic acid, pyridine, tetrahydrofuran, DMF, 1,1-dichloroethane, methylene chloride, benzene, diethyl ether, diethylene glycol, glycol dimethyl ether, and the like.

Particularly preferred combinations of oxidizing agents and solvents for step "b." are selected from the group consisting of DDQ, DDQ with $O_2$, $O_2$, aqueous permanganates, aqueous dichromates, $Cr_3$ in glacial acetic acid or pyridine, pyridinium chlorochromate, pyridinium dichromate, copper turnings heated to a temperature of about 200°–300° C., and the like.

Specific examples of oxidizing agents that are particularly useful for direct addition to the reaction mixture at the end of the cyclization step "a.", without the intervening isolation or purification of specific compounds in the cyclization reaction mixture, include: (1) treatment with oxygen and dichloro-dicyanobenzoquinone ("DDQ") or another co-oxidant and (2) stirring the mixture in a vessel that is open to the air, particularly in the presence of an acid. In such cases, oxidation may proceed at a satisfactory rate, as commonly occurs with the first method, or the reaction may occur dependably but at rate that may be significantly slower, as sometimes occurs with the second method. Thus, the rate of the reaction is often influenced by the type and combination of oxidizing agent, with or without the presence of a solvent.

The temperature of the reaction mixture during the oxidation step "b." can vary widely depending upon the oxidizing agent being used. For example, when copper metal is being used as the oxidizing agent, vapors from the reaction mixture are generally passed through a tube packed with copper turnings, which have been heated to about 200°–300° C. to accomplish the desired reaction. When other oxidizing agents are used, however, the temperature is typically maintained in the range of about 0° to 100° C. and, preferably, is allowed to remain at about room temperature.

The time required for the oxidation reaction of step "b." will depend to a large extent on the temperature used and the relative reactivities of the starting materials but, preferably, is about room temperature. The oxidation reaction of step "b." can be carried out in the presence of gases at a pressure both above and below atmospheric pressure. Most frequently, however, the reaction is carried out at a pressure about equal to atmospheric pressure.

The resulting product, a 5,15-diarylbenzo-chlorin-7-one compound of formula (I), can be isolated by any conventional method, such as by drowning out in a non-solvent, precipitating out, extraction with any immiscible liquid, evaporation of a solvent, or some combination of these or other conventional methods. Typically, the benzochlorinone compound of formula (I) may then be purified by any one or a combination of known purification techniques, such as recrystallization, various forms of chromatography, trituration with a non-solvent or a partial solvent, vacuum distillation, countercurrent extraction techniques, and the like.

The benzochlorinone compound of formula (I) can be demetallated after the oxidizing step "b." Alternatively, the metal M can be removed from the compounds making up the cyclization reaction mixture after the cyclizing step "a." In most cases, however, the metal M is removed after the oxidation step "b." for the sake of convenience. In any event, the step "a." of cyclizing the vinylformyl starting material of formula (III) will generally not occur if the vinylformyl compound of formula (II) has already been demetallated. Thus, it is believed to be important to have the metal M still present during the cyclizing step "a."

Whether the benzochlorinone compound of formula (I) or the compounds in the cyclization reaction mixture after the cyclizing step "a." are being demetallated, the reaction conditions are usually the same or very similar. Typical demetallating reagents used for this purpose include mineral acids, such as sulfuric acid and hydrochloric acid; carboxylic acids, such as acetic acid, trifluoroacetic acid, trichloroacetic acid, α-bromopropionic acid, and 15% sulfuric acid in trifluoroacetic acid; and thiols such as $H_2S$, 1,3-propanedithiol and $H_2S$-saturated trifluoroacetic acid. Preferably, the demetallating agent is selected from the group consisting of $CH_3COOH$, $CF_3COOH$, $H_2SO_4$, $H_2S$, 1,3-propanedithiol, and mixtures thereof. Examples of suitable mixtures of demetallating agents include: (1) 15% sulfuric acid in trifluoroacetic acid, (2) trifluoroacetic acid and $H_2S$, and (3) trifluoroacetic acid and 1,3-dipropanedithiol. Preferred mixtures include (1) 15% sulfuric acid in trifluoroacetic acid and (2) $H_2S$-saturated trifluoroacetic acid.

The above demetallating agents can sometimes be used in combination with a suitably non-reactive solvent. Examples of useful solvents include water; alcohols, such as ethanol, methanol, iso-propanol and the like; haloalkanes such as methylene chloride, 1,1-dichloroethane and the like; nitrogen-containing solvents such as DMF, tetrahydrofuran and the like; relatively unreactive aromatic compounds such as benzene, toluene and the like; and ethers such as diethyl ether, diethylene glycol, and glycol dimethyl ether. Most preferably, however, the demetallating agent is used without a solvent.

The temperature of the reaction mixture during the demetallating process can vary widely but, typically, is maintained in the range of about 20° to 120° C. For example, refluxing acetic acid can be used as a demetallating agent in some circumstances, which would provide a temperature of about 118° C. However, the demetallating reaction is most preferably carried out at about room temperature.

The time required for demetallation varies widely, depending on the temperature used and the relative reactivities of the starting materials, particularly the demetallating agent. For example, when 15% sulfuric acid in trifluoroacetic acid is used as the demetallating agent, the reaction typically takes place from about five minutes to about an hour. On the other hand, when $H_2S$-saturated trifluoroacetic acid is used as the demetallating agent, the time of reaction generally varies from about one hour to about four days.

The reaction can be carried out above or below atmospheric pressure. Preferably, the reaction is carried out at a pressure about equal to atmospheric pressure.

Straightforward procedures can be used to isolate the demetallated product, such as neutralization of the reaction mixture, extraction with any immiscible liquid (such as methylene chloride), eluting on a silica gel column or other types of chromatography, drowning out in a non-solvent, precipitating out or otherwise crystallizing, evaporation of solvent, or some combination of these or other conventional methods. Preferred methods of isolating the desired demetallated compound of formula (II) include chromatography and/or crystallization. If further purification of the demetallated product is desired, it may be subjected to additional purification procedures, such as recrystallization, eluting on a silica gel chromatography column, and combinations of these methods.

The 5,15-diarylbenzochlorin-7-one compounds of the invention are useful as photosensitizers in photodynamic therapy (PDT). Specifically, these compounds are useful in sensitizing neoplastic cells or other abnormal tissues to destruction by irradiation with visible light. Upon photoactivation, the energy of photoactivation is believed to be transferred to endogenous oxygen, thus converting it to singlet oxygen. This singlet oxygen is thought by some to be responsible for the observed cytotoxic effect. Alternatively, there may be direct electron transfer from the photoactivated molecule. In addition, the photoactivated forms of porphyrin are able to fluoresce, and this fluorescence can aid in imaging a tumor.

Typical indications known in the art include diagnosis and destruction of tumor tissue in solid tumors, such as those of bronchial, cervical, esophageal or colon cancer; dissolution of plaques in blood vessels (see, e.g., U.S. Pat. No. 4,512,762, which is hereby incorporated by reference); treatment of topical conditions such as acne, athlete's foot, warts, papilloma and psoriasis; and treatment of biological products, such as blood for transfusion to eliminate infectious agents.

The compounds of the invention can be formulated into pharmaceutical compositions for administration to the subject or applied to an in vitro target using techniques generally known in the art. A summary of such pharmaceutical compositions may be found, for example, in Remington's Pharmaceutical Sciences, Mack Publishing Co., Easton, Pa. The compounds of the invention can be used singly or as components of mixtures.

Generally, for the diagnosis or treatment of solid tumors, the compound of the invention, labeled or unlabeled, is administered systemically, such as by injection. Injection may be intravenous, subcutaneous, intramuscular, or even intraperitoneal. Injectables can be prepared in conventional forms, either as liquid solutions or suspensions, solid forms suitable for solution or suspension in a liquid prior to injection, or as emulsions. Suitable excipients are, for example, water, saline, dextrose, glycerol and the like. Of course, these compositions may also contain minor amounts of nontoxic, auxiliary substances, such as wetting or emulsifying agents, pH buffering agents, and so forth.

Systemic administration can be implemented through implantation of a slow release or sustained release system, by suppository, or, if properly formulated, orally. Formulations for these modes of administration are well known in the art, and a summary of such methods may be found, for example, in Remington's Pharmaceutical Sciences (supra).

If treatment is to be localized, such as for the treatment of superficial tumors or skin disorders, the compound can be administered topically using standard topical compositions, such as lotions, suspensions, or pastes.

The quantity of the compound to be administered depends upon the choice of active ingredient, the condition to be treated, the mode of administration, the individual subject, and the judgment of the practitioner. Depending on the specificity of the preparation, smaller or larger doses may be needed. For compositions that are highly specific to target tissues, such as those with a highly specific monoclonal immunoglobulin preparation or a specific receptor ligand, dosages in the range of 0.05–1 mg/kg are suggested. For compositions that are less specific to the target tissue, larger doses, up to 1–10 mg/kg may be needed. The foregoing ranges are merely suggestive, as the number of variables in regard to an individual treatment regime is large, and considerable excursions from these recommended values are not uncommon.

In addition to in vivo use, the compounds of the invention can be used in the treatment of materials in vitro to destroy harmful viruses or other infectious agents. For example, blood plasma or blood that is to be used for transfusion or banked for future transfusion, can be treated with the compounds of the invention and irradiated to effect sterilization. In addition, biological products such as Factor VIII, which are prepared from biological fluids, can be irradiated in the presence of the compounds of the invention to destroy contaminants.

Because the compounds of the invention have a carbonyl group (the β-keto group) conjugated with the double bonds of the benzochlorin nucleus, they exhibit a marked bathochromic shift and an improved intensification of the Q band occurring at the longest wavelength, when compared with previously reported β-alkyl-substituted 5,15-diphenyl benzochlorins lacking the corresponding keto group. These characteristics thus make possible greater penetration of activating light through normal tissue.

Further, because the aryl ring groups in the 5- and 15-meso positions can be substituted, either symmetrically or asymmetrically, the compounds of the invention can be "fine tuned" to produce a desired set of biological effects when administered to a subject in need of photodynamic therapy. Further still, the invention provides methods for synthesizing these 5,15-diarylbenzochlorin-7-one compounds in an efficient manner with few by-products or isomeric impurities.

The invention will be further clarified by the following example, which is intended to be purely illustrative of the invention.

EXAMPLE 1

Synthesis of Cu(II) 5,15-Diphenylbenzochlorin-7-one

Preparing Cu(II) 5, 15-Diphenyl-10-(2-formylvinyl) porphyrin

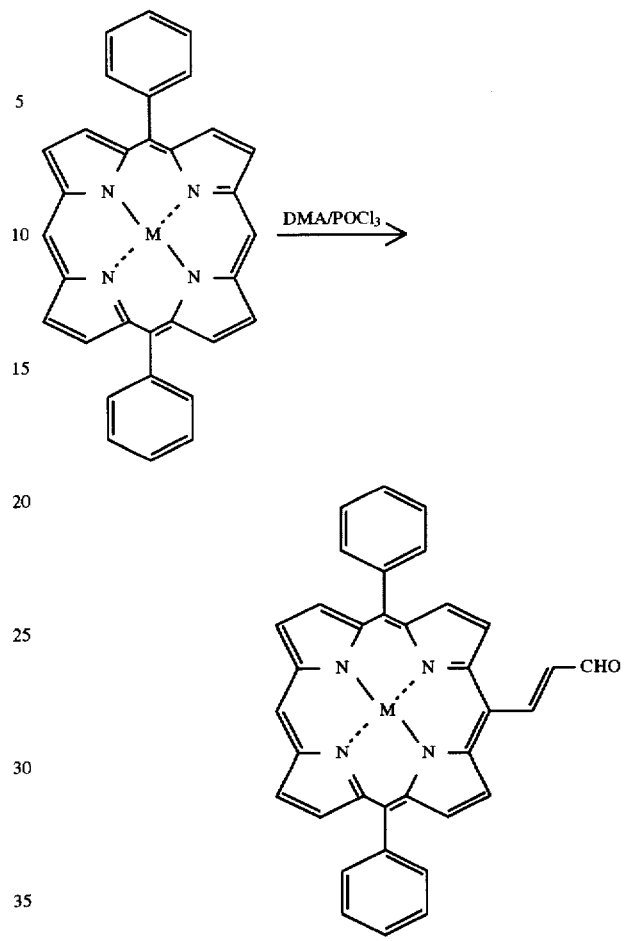

3-(Dimethylamino)acrolein (1.91 ml; 19 mmol) was dissolved in 1,2-dichloroethane (30 ml), and the solution was cooled to 0° C. under a nitrogen atmosphere. To this solution was added, dropwise, freshly distilled phosphorous oxychloride (0.92 ml; 9.87 mmol). The mixture was warmed to 50° C. and stirred for 30 minutes. About 100 mg (0.19 mmol) of Cu(II) 5,15-diphenylporphyrin was dissolved in 1,2-dichloroethane (21 ml) and added to the reaction mixture. The reaction mixture was then sonicated for 4 hours. Saturated aqueous sodium acetate (140 ml) was added, and the mixture was stirred vigorously for 16 hours, then poured into water (200 ml), and extracted with dichloromethane (3×100 ml). The combined organic extracts were dried over anhydrous sodium sulfate. Evaporation of the solvent in vacuo, followed by chromatography (silica gel, dichloromethane)

of the residue gave Cu(II) 5,15-diphenyl-10-(2-formylvinyl)-porphyrin (39 mg; 35%).

UV-vis: λ 422, 542, 590 nm in CH$_2$Cl$_2$; HRMS (EI) for C$_{35}$H$_{22}$N$_4$OCu(M$^+$) calcd. 577.1089; found 577.1091.

Cyclization and Oxidation Reaction:

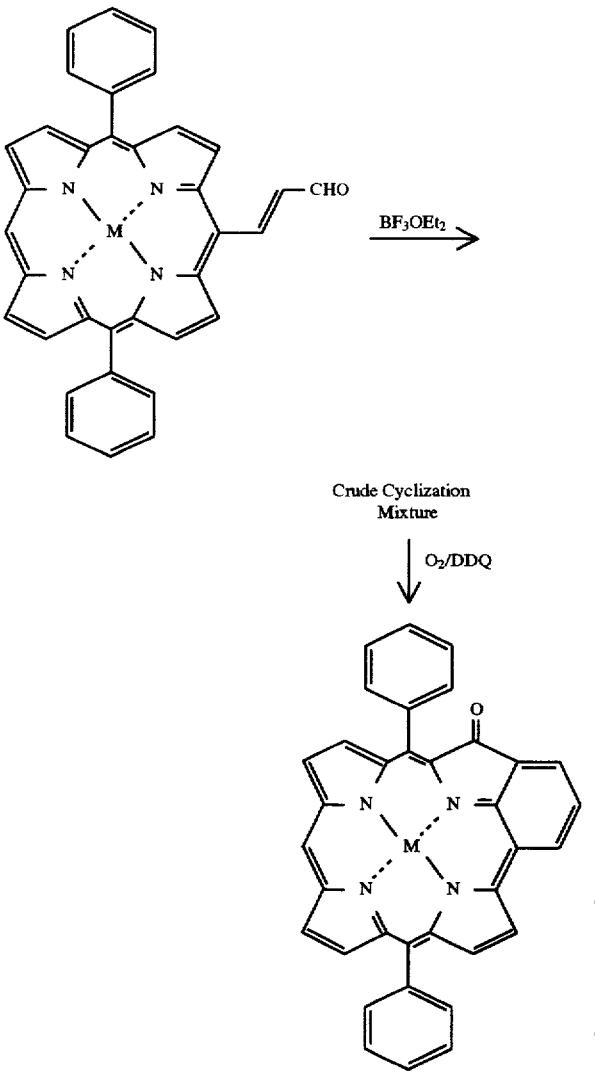

A. Cyclization

Cu(II) 5,15-diphenyl-10-(2-formylvinyl)porphyrin (10 mg; 17 μmol) was dissolved in dry 1,2-dichloromethane (10 ml). To the stirred solution was added, under a nitrogen atmosphere, freshly distilled boron trifluoride etherate (25 μl; 200 μmol). The resulting green solution was stirred for two hours. The reaction mixture was poured into water (50 ml) and was extracted with dichloromethane (3×20 ml). The combined organic extracts were washed with saturated aqueous sodium hydrogen carbonate (3×50 ml) and then water (3×50 ml). After drying over anhydrous sodium sulfate, the solvent was evaporated in vacuo to give 6.3 mg (65%) of crude product.

UV-vis: λ 424, 442, 574, 622, 672 nm in CH$_2$Cl$_2$; HRMS (FAB) for C$_{35}$H$_{21}$N$_4$Cu(M$^{+1}$) calcd. 560.1062; found 560.1063.

B. Oxidation

The crude cyclization mixture from above (10 mg; 18 μmol) was dissolved in dichloromethane (10 ml), and oxygen (O$_2$) was bubbled through the solution for five minutes. 5,6-Dicyano-1,4-benzoquinone (DDQ) (40 mg; 0.18 mmol) was added, and the solution was stirred for an additional two hours. The solution was then filtered through a short column of neutral alumina. The solvent was evaporated from the eluent, in vacuo, and the residue was chromatographed (silica gel, dichloromethane) to give 3.7 mg of the desired ketone product. Cu(II) 5,15-diphenylbenzochlorin-7-one (37%).

UV-vis: λ 372, 416, 464, 488, 688(s), 730 nm in CH$_2$Cl$_2$; HRMS (EI) for C$_{35}$H$_{22}$N$_4$OCu(M$^+$) calcd. 575.0933; found 575.0924.

EXAMPLE 2

Demetallation of CU(II) 5,15-Diphenylbenzochlorin-7-one

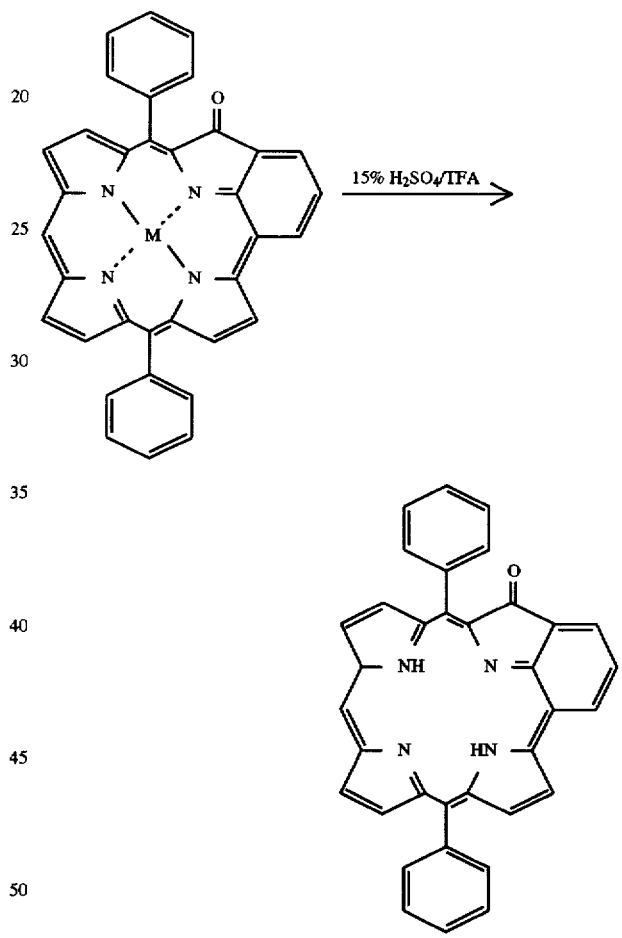

Cu(II) 5,15-diphenylbenzochlorin-7-one (5 mg; 9 μmol) was placed in a flask under an inert atmosphere. A mixture of 15% (v/v) H$_2$SO$_4$ in trifluoroacetic acid (2 ml) was added, and the resulting solution was stirred for five minutes. The mixture was then poured into water (50 ml) and extracted with dichloromethane (3×20 ml). The combined organic phases were washed with saturated aqueous sodium bicarbonate (3×50 ml), washed with water (3×50 ml), and finally dried over anhydrous potassium carbonate. Evaporation of the solvent in vacuo, followed by chromatography of the residue on neutral alumina eluting with dichloromethane, gave 5,15-diphenylbenzochlorin-7-one (3 mg; 67%).

H$^1$ NMR (CDCl$_3$) δ 7.65–7.69 (m, 8 H phenyl+1 H benzo), 7.78 (d, J=4.4 Hz, 1 H), 7.89 (d, J=3.33 Hz, 1 H), 7.93 (d, J=1.92, 1 H), 7.95 (d, J=1.37 Hz, 1H), 8.19 (d, J=3.8 Hz, 1 H), 8.21 (d, J=3.7 Hz, 1 H), 8.29 (d, J=6.25 Hz, 1 H), 8.36 (d, J=4.36 Hz, 1 H, 8.73 (d, J=3.76 Hz, 1 H), 8.85 (s, 1 H), 9.31 (d, J=8 Hz, 1 H);

UV-vis: λ 378, 456, 612, 658, 746 nm in $CH_2Cl_2$; HRMS (E1) for $C_{35}H_{22}N_4O$ ($M^+$) calcd. 514.1794; found 514.1790.

EXAMPLE 3

Synthesis of Ni(II) 5,15-Diphenylbenzochlorin-7-one

Preparing Ni(II) 5 15-Diphenyl-10-(2-formylvinyl) porphyrin

Ni(II) 5,15-diphenylporphyrin (100 mg; 0.19 mmol) was treated with 3-(dimethylamino)acrolein and phosphorous oxychloride, using the identical procedure as described above for Cu(II) 5,15-diphenyl-10-(2-formylvinyl) porphyrin to give the corresponding Ni(II) compound (32 mg; 29%).

UV-vis: λ 420, 540, 588 nm in $CH_2Cl_2$; MS (E1) 572 (100).

A. Cyclization Reaction:

Ni(II) 5,15-diphenyl-10-(2-formylvinyl)porphyrin (10 mg; 18 μmol) was dissolved in dry dichloromethane (10 ml). To the stirred solution, under nitrogen, was added freshly distilled boron trifluoride etherate (25 μl; 200 μmol). After stirring for two hours, the reaction mixture was poured into water (50 ml) and extracted with dichloromethane (3×20 ml). The combined organic extracts were washed with saturated aqueous sodium hydrogen carbonate (3×50 ml) and then water (3×50 ml). After drying over anhydrous sodium sulfate, the solvent was evaporated in vacuo to give 7 mg (70%) of crude product.

$H^1$ NMR ($CDCl_3$) δ 5.78 (d, J=6.81 Hz, 1 H), 6. 03 (t, J=7.5 Hz, 1 H), 6.09 (s, 1 H), 7.56 (t, J=7.34 Hz, 2 H), 7.62 (d, J=4.8 Hz, 1 H), 7.66–7.74 (m, 7 H), 7.82 (d, J=8.1 Hz, 1 H), 8.1 (d, J=4.5 Hz, 1 H), 8.24 (d, J=4.7 Hz, 1 H), 8.26 (d, J=4.7 Hz, 1 H), 8.29 (d, J=4.5 Hz, 1 H), 8.44 (d, J=4.9 Hz, 1 H), 8.78 (s, 1 H); UV-vis: λ 420, 522, 560, 668 nm in $CH_2Cl_2$; HRMS (FAB) for $C_{35}H_{21}N_4Ni(M^+)$ calcd. 555.1119; found 555.1114.

B. Oxidation Reaction

The crude cyclization mixture from above (5 mg; 9 μmol) was dissolved in dichloromethane (10 ml), and oxygen ($O_2$) was bubbled through the solution for five minutes. DDQ (20 mg; 0.9 μmol) was added. After two hours, the reaction mixture was filtered through a short column of neutral alumina. The solvent was evaporated from the eluent in vacuo. Chromatographic separation (silica gel, 10% ethyl acetate in dichloromethane) of the residue gave 1.5 (29%) mg of the desired ketone product, Ni(II) 5,15-diphenylbenzochlorin-7-one.

$H^1$ NMR ($CDCl_3$) δ 7.57 (t, J=7.42 Hz, 1 H), 7.64–7.68 (m, 8 H), 7.82 (d, J=1.75, 1 H), 7.84 (d, J=1.33 Hz, 1 H), 7.95 (d, J=4.71 Hz, 1 H), 8.02 (d, J=4.53 Hz, 1 H), 8.14 (d, J=6.65 Hz, 1 H), 8.29 (d, J=4.64 Hz, 1 H), 8.31 (d, J=4.83 Hz, 1 H), 8.41 (d, J=4.83 Hz, 1 H), 8.72 (d, J=4.9 Hz, 1 H), 8.88 (s, 1 H), 9.07 (d, J=7.6 Hz, 1 H); FTIR: υ 1731 $cm^{-1}$ ($CO_{str}$); UV-vis: λ 370, 448, 474, 676, 730 nm in $CH_2Cl_2$; HRMS (E1) for $C_{35}H_{20}N_4ONi(M^+)$ calcd. 570.0990; found 570.0981.

EXAMPLE 3

Testing of Compounds

Each of the following compounds were dissolved in dichloromethane at the specified concentration:

(1) Cu(II) 5,15-diphenylbenzochlorin-7-one (8 μM);

(2) Ni(II) 5,15-diphenylbenzochlorin-7-one (13 μM); and (3) 5,15-Diphenylbenzochlorin-7-one (demetallated) (1.5 μM).

Figure 2:
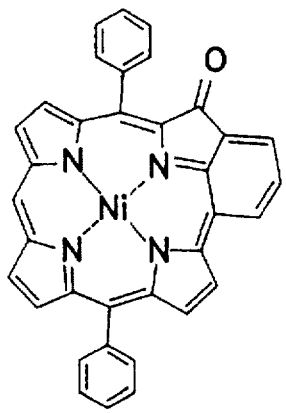
FIG. 2 shows the absorbance spectrum of Ni(II) 5,15-diphenylbenzochlorin-7-one.
Figure 2:
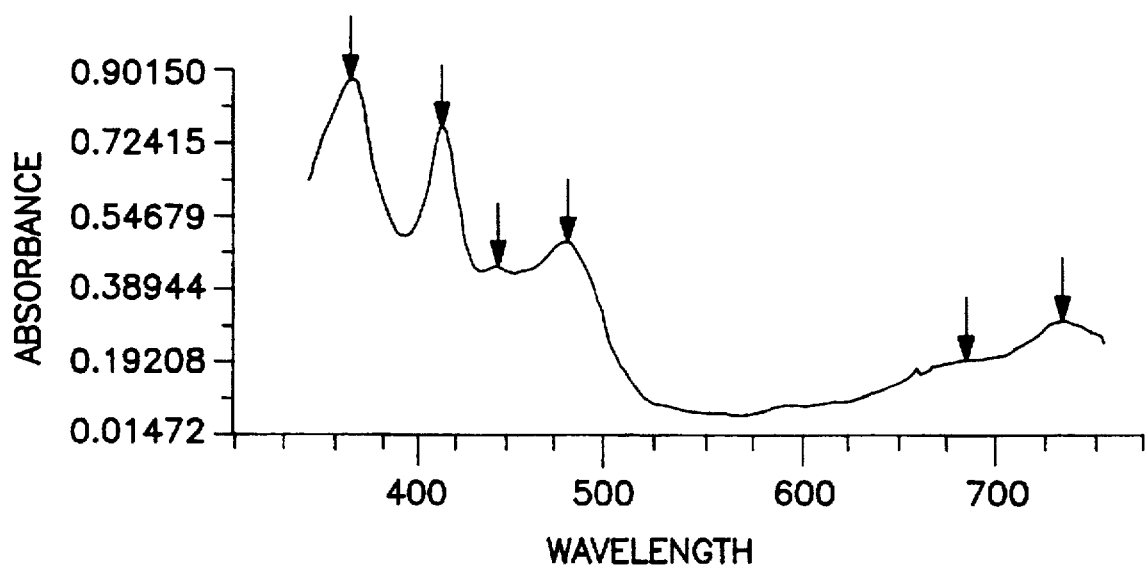
Figure 3:
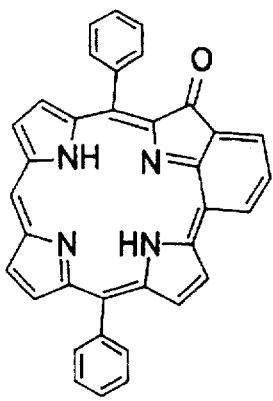
FIG. 3 shows the absorbance spectrum of demetallated 5,15-diphenylbenzochlorin-7-one.
Figure 3:
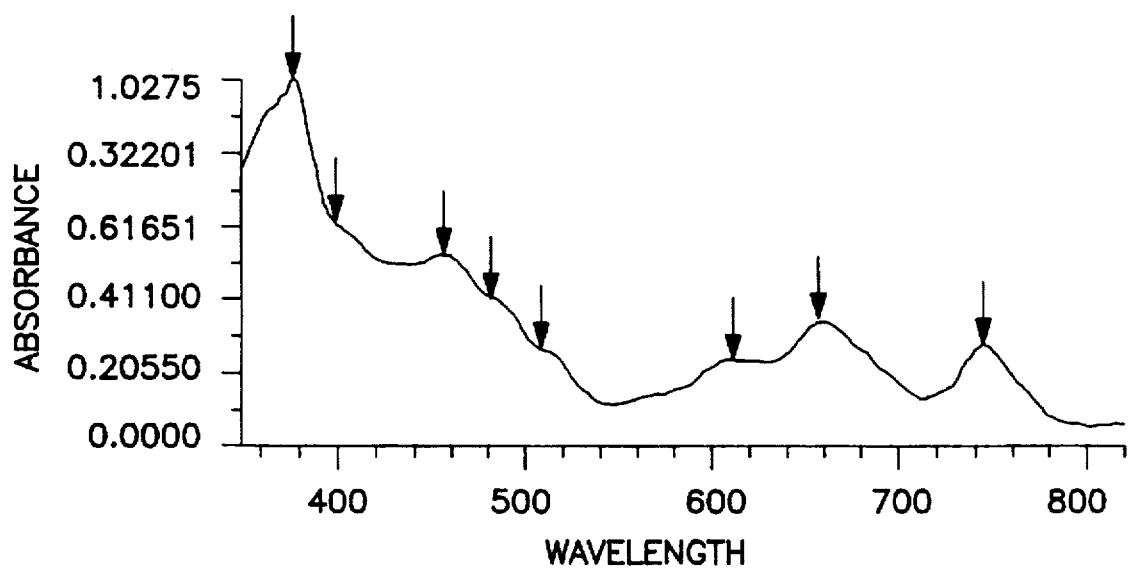

Using a pathlength of 1 cm, the absorbance was measured as a function of wavelength, and the results are recorded for each of the above compounds in FIGS. 1, 2 and 3 respectively.

For Cu(II) 5,15-diphenylbenzochlorin-7-one, absorption maxima were noted at the following wavelengths:

| $λ_{max}$ | Absorbance |
|---|---|
| 374 nm | 0.56 |
| 416 nm | 0.28 |
| 464 nm | 0.32 |
| 488 nm | 0.35 |
| 670 nm | 0.15 |
| 732 nm | 0.25 |

For Ni(II) 5,15-diphenylbenzochlorin-7-one, absorption maxima were noted at the following wavelengths:

| $λ_{max}$ | Absorbance |
|---|---|
| 370 nm | 0.88 |
| 416 nm | 0.77 |
| 444 nm | 0.43 |
| 480 nm | 0.49 |
| 682 nm | 0.21 |
| 732 nm | 0.30 |

For 5,15-diphenylbenzochlorin-7-one (demetallated), absorption maxima were noted at the following wavelengths:

| $λ_{max}$ | Absorbance |
|---|---|
| 378 nm | 1.03 |
| 400 nm | 0.63 |
| 456 nm | 0.54 |
| 482 nm | 0.41 |
| 508 nm | 0.27 |
| 612 nm | 0.23 |
| 658 nm | 0.33 |
| 746 nm | 0.26 |

The demetallated species shown directly above, in particular, showed strong absorption maxima across the entire range of the visible spectrum (from about 300 to 760 nm). Because of the broad range of strong absorption maxima, a large number of different wavelengths can be used for photoactivating the molecule during photodynamic therapy.

We claim:

1. A method for synthesizing a 5,15-diarylbenzochlorin-7-one having the formula

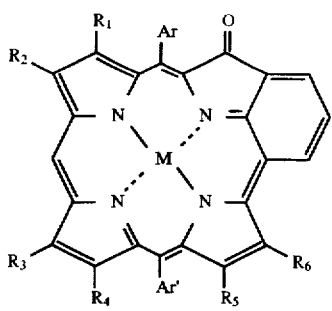

(I)

or the demetallated form thereof wherein M is a metal selected from the group consisting of Ni(II), Cu(II), Zn, Sn, Ge, Si, Ga and Al;

each of $R_1$ through $R_6$ is independently a hydrogen atom, a lower alkyl group, a lower alkyl carboxylic acid or acid ester group or, taken together with another ring, ring substituent, or meso-substituent, forms a fused 5- or 6-membered ring; and Ar and Ar' are aromatic rings, which may be the same or different; comprising the steps of:

a. cyclizing a meso-(formylvinyl) 5,15-diarylporphyrin having the formula (III)

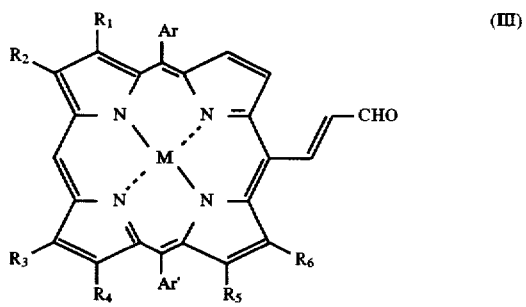

(III)

or a demetallated form thereof to form a cyclization reaction mixture; and b. oxidizing said cyclization reaction mixture to form the 5,15-diarylbenzochlorin-7-one of formula (I) or said demetallated form.

2. The method of claim 1 wherein the compound of formula (I) is in demetallated form.

3. The method of claim 1 wherein said compound of formula (III) is in demetallated form.

4. The method of claim 1 wherein M is Ni or Cu.

5. The method of claim 1 wherein $R_1$ through $R_6$ are independently hydrogen, methyl, ethyl, or lower alkyl esters.

6. The method of claim 1 wherein Ar and Ar' have the structure:

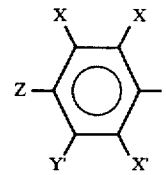

wherein X, X', Y, Y' and Z are independently hydrogen, halogen, lower alkyl, lower alkoxy, hydroxy, carboxylic acid ester, sulfonic acid ester, substituted or unsubstituted amino, cyano, nitro, or a biologically active group.

7. The method of claim 6 wherein at least one of X, X', Y, Y' and Z is a biologically active group or a group that increases the amphiphilic nature of the molecule.

8. The method of claim 1 wherein said cyclizing step a. comprises treating the meso-(formylvinyl) 5,15-diarylporphyrin of formula (III) or a demetallated form thereof with at least one reagent selected from the group consisting of $BF_3O(C_2H_5)_2$, $F_3COOH$, $CCl_3COOH$, $H_2SO_4$, $SnCl_4$ and Cu(II).

9. The method of claim 1 wherein, in said cyclizing step a., said meso-(formylvinyl) 5,15-diarylporphyrin of formula (III) or a demetallated form thereof is reacted with said reagent for a time from about 15 minutes to about 3 hours.

10. The method of claim 1 wherein said cyclizing step a. takes place at room temperature and in an atmosphere enriched with respect to nitrogen gas.

11. The method of claim 1 wherein said oxidizing step comprises treating said cyclization reaction mixture with an oxidizing agent selected from the group consisting of DDQ, DDQ with $O_2$, $O_2$, aqueous permanganates, aqueous dichromates, $CrO_3$ in glacial acetic acid or pyridine, pyridinium chlorochromate, pyridinium dichromate, copper turnings heated to a temperature of about 200°–300° C.

* * * * *

UNITED STATES PATENT AND TRADEMARK OFFICE
CERTIFICATE OF CORRECTION

PATENT NO. : 5,780,622  
DATED : July 14, 1998  
INVENTOR(S) : David Dolphin, et al.

Page 1 of 2

It is certified that error appears in the above-identified patent and that said Letters Patent is hereby corrected as shown below:

On the title page: Item [56] add the following:

U. S. PATENT DOCUMENTS

| EXAMINER INITIAL | | PATENT NUMBER | | | | | | | ISSUE DATE | PATENTEE | CLASS | SUBCLASS | FILING DATE IF APPROPRIATE |
|---|---|---|---|---|---|---|---|---|---|---|---|---|---|
| | | 4 | 9 | 8 | 8 | 8 | 0 | 8 | 01/29/91 | Morgan et al. | | | |
| | | 5 | 1 | 7 | 1 | 7 | 4 | 9 | 12/15/92 | Levy et al. | | | |
| | | | | | | | | | | | | | |

OTHER DOCUMENTS

| | | |
|---|---|---|
| | Arnold et al., "Wittig Condensation Products from Nickel meso-Formyl-octaethylporphyrin and -aetioporphyrin 1 and Some Cyclisation Reactions," *J.C.S. Perkin 1*, 1660-70 (1978) |
| | Barloy et al., "Anomalous Cyclization Reactions of B-Formyl Porphyrins," *J. Org. Chem.*, publication date unknown |
| | Boyle et al., *J. Chem. Soc., Chem. Commun.* 2463-4. |
| | Boyle et al., "5-15-Diphenyl-7-oxobenzochlorins, Novel Long-wavelength Absorbing Photosensitizers for Photodynamic Therapy, *J.Chem. Soc. Chem. Commun.*, 2463-64 (1994) |

UNITED STATES PATENT AND TRADEMARK OFFICE
CERTIFICATE OF CORRECTION

PATENT NO. : 5,780,622
DATED : July 14, 1998
INVENTOR(S) : David Dolphin, et al.

It is certified that error appears in the above-identified patent and that said Letters Patent is hereby corrected as shown below:

OTHER DOCUMENTS

| | |
|---|---|
| | Callot et al., "Unexpected Routes to Naphtoporphyrin Derivatives," *Tetrahedron*, 46:15, 5253-62 (1990) |
| | Chang et al., "Migratory Aptitudes in Pinacol Rearrangement of vic-Dihydroxychlorins," *J. Heterocyclic Chem.*, 22, 1739-41 (1985) |
| | Gunter, "5,15-Diaryl Substituted Benzochlorins--Synthesis and Structure," *Tetrahedron*, 47, 7853-68 (1991) |
| | Osuka et al., "Synthesis of Benzochlorin Monomer, Dimer, and Porphyrin-Benzochlorin Heterodimer from 5-Aryl-and 5,15-Diaryl-octaethylporphyrins," *Bull. Chem. Soc. Jpn.*, 65, 3322-30 (1992) |
| | Vicente et al., "Vilsmeier Reactions of Porphyrins and Chlorins with 3-(Dimethylamino)acrolein to Give meso-(-2-Formylvinyl)porphyrins: New Syntheses of Benzochlorins, Benzoisobacteriochlorins, and Benzobacteriochlorins and Reductive Coupling of Porphyrins and Chlorins Using Low-Valent Titanium Complexes," *J. Org. Chem.* 56, 4407-18 (1991) |
| | Vicente et al., "Efficient New Syntheses of Benzochlorins, Benzoisobacteriochlorins, and Benzobacteriochlorins," *Tetrahedron Letters*, 31, 1365-68 (1990) |

Signed and Sealed this

Fourth Day of May, 1999

Attest:

Q. TODD DICKINSON

*Attesting Officer*    *Acting Commissioner of Patents and Trademarks*